US00PP32840P2

(12) United States Plant Patent
Boxriker

(10) Patent No.: US PP32,840 P2
(45) Date of Patent: Feb. 23, 2021

(54) ***OSTEOSPERMUM* PLANT NAMED 'KLEOE20555'**

(50) Latin Name: ***Osteospermum ecklonis* Norl.**
Varietal Denomination: KLEOE20555

(71) Applicant: Klemm+Sohn GmbH & Co. KG, Stuttgart (DE)

(72) Inventor: Maike Boxriker, Schwäbisch Gmünd (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/867,148

(22) Filed: May 5, 2020

(51) Int. Cl.
*A01H 5/02* (2018.01)
*A01H 6/14* (2018.01)

(52) U.S. Cl.
USPC ..... Plt./360
CPC ..... *A01H 6/148* (2018.05)

(58) Field of Classification Search
USPC ..... Plt./360
CPC ..... A01H 6/148; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Osteospermum* plant particularly distinguished by having red ray florets with red stripes, and an upright growth habit, is disclosed.

1 Drawing Sheet

Genus and species: *Osteospermum ecklonis* Norl.
Variety denomination: 'KLEOE20555'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE20555'. 'KLEOE20555' originated from a cross-pollination conducted in August/September 2013 in Stuttgart, Germany between the proprietary female *Osteospermum* variety 'OE-2015-2178' (unpatented) and the proprietary male *Osteospermum* variety 'OE-2014-1322', also known as 'KLEOE13206' (unpatented).

The seeds from the cross were sown and plants were grown in a greenhouse for evaluation, where an individual plant designated 'KLEOE20555' was selected from the group of plants in May 2016 in Stuttgart, Germany. In September 2016 in Stuttgart, Germany, 'KLEOE20555' was first vegetatively propagated by vegetative terminal cuttings. 'KLEOE20555' was found to reproduce true to type in successive generations of asexual propagation via vegetative terminal cuttings.

SUMMARY

The following are the most outstanding and distinguishing characteristics of this new variety when grown under normal horticultural practices in Stuttgart, Germany.

1. Flowers having red ray florets with red stripes; and
2. An upright growth habit.

DESCRIPTION OF THE PHOTOGRAPH

This new *Osteospermum* plant is illustrated by the accompanying photograph which shows the plant's overall plant habit including form, foliage, and flowers. The photograph is a top view of three 9-week-old plants grown in a greenhouse in Stuttgart, Germany in April 2019. The colors shown are as true as can be reasonably obtained by conventional photographic procedures.

DESCRIPTION OF THE NEW VARIETY

The following detailed descriptions set forth the distinctive characteristics of 'KLEOE20555'. The data which define these characteristics were collected in Latina, Italy in March 2020 on 20-week-old plants. Color references are to The R.H.S. Colour Chart of The Royal Horticultural Society of London (R.H.S.), 5$^{th}$ edition (2007).

Classification:
- *Family.*—Asteraceae.
- *Botanical.*—*Osteospermum ecklonis.*
- *Common.*—*Osteospermum.*
- *Designation.*—'KLEOE20555'.

Parentage:
- *Female parent.*—The proprietary *Osteospermum* 'OE-2015-2178' (unpatented).
- *Male parent.*—The proprietary male *Osteospermum* variety 'OE-2014-1322' (unpatented).

Plant:
- *Form and habit.*—Herbaceous perennial but usually cultivated as an annual; not frost resistant.
- *Growth habit.*—Upright.
- *Branching habit.*—Upright.
- *Height* (*from top of soil, including inflorescence*).—29.8 cm. Width (including inflorescences): 26.7 cm. Propagation: Vegetative terminal cuttings. Time to produce a finished flowering plant: 9 weeks. Time to initiate and develop roots: 4 weeks. Root description: Fine, white RHS 155A.

Stems:
- *Total number of branches per plant* (*calculated at the base of the plant*).—6.
- *Length.*—27.5 cm.
- *Diameter.*—0.6 cm.

*Internode length.*—3.3 cm.
*Color.*—RHS 137D (Green).
*Texture.*—Smooth.
*Anthocyanin.*—Present, at apex of stems and under flowers, RHS 53B (Red).

Leaves:
*Arrangement.*—Alternate.
*Shape.*—Obovate.
*Apex.*—Acute.
*Base.*—Acute.
*Margin.*—Spiny.
*Immature color.*—Upper surface: RHS N137C (Green). Lower surface: RHS 138A (Green).
*Mature color.*—Upper surface: RHS N137A (Green). Lower surface: RHS 137C (Green).
*Length.*—8.4 cm.
*Width.*—3.3 cm.
*Texture and appearance.*—Upper surface: Leathery. Lower surface: Leathery with fine hairs.
*Petioles.*—Absent.
*Venation pattern.*—Pinnate.
*Venation color.*—Upper surface: RHS N137A (Green). Lower surface: RHS 137C (Green).

Flower buds:
*Shape.*—Round-ovoid.
*Apex.*—Acute.
*Length.*—1.7 cm.
*Diameter.*—0.8 cm.
*Color (at tight bud just before the ray florets unfold).*—RHS 138B (Green).
*Texture.*—Smooth.

Inflorescence:
*Type.*—Composite, single.
*Blooming habit.*—Upright with flower stems.
*Quantity of inflorescences per plant.*—25 open flowers per plant.
*Lastingness of the inflorescences on the plant.*—12 to 15 days.
*Fragrance.*—Slightly present, sweet.
*Inflorescence diameter.*—6.1 cm.
*Inflorescence depth.*—0.9 cm.
*Disc diameter.*—1.4 cm.

Disc floret:
*Quantity per inflorescence.*—89.
*Shape.*—Tubular.
*Tube color (closed and mature).*—Basal part is RHS NN155A (White), middle part is RHS N65 (Red-Purple), and the apical part is RHS N79A (Purple).
*Length.*—0.7 cm.
*Diameter (at apex).*—0.1 cm.
*Apex.*—Acute.
*Apex color.*—RHS N79A (Purple).
*Base.*—Acute.
*Base color.*—RHS NN155A (White).
*Margin.*—Entire.

Ray floret:
*Quantity per inflorescence.*—18.
*Shape.*—Oblanceolate.
*Color.*—Upper surface: RHS 45B (Red) with 46A (Red) stripes. Lower surface: RHS 59C (Red-Purple) with 45B (Red) stripes.
*Length.*—2.9 cm.
*Width.*—0.8 cm.
*Apex.*—Obtuse.
*Base.*—Entire.
*Margin.*—Entire.
*Texture (upper and lower surfaces).*—Smooth.
*Peduncle.*—Length: 7.6 cm. Diameter: 0.2 cm. Texture: Smooth with hairs. Color: Basal part is RHS 137D (Green) and the apex part is RHS 53D (Red).

Phyllaries:
*Texture.*—Smooth with fine hairs.
*Color.*—RHS 143A (Green).
*Arrangement.*—Single.
*Observed quantity per plant.*—19.
*Shape.*—Lanceolate.
*Color.*—Upper surface: RHS 143A (Green). Lower surface: RHS 144A (Yellow-Green).
*Length.*—1.2 cm.
*Width.*—0.2 cm.
*Apex.*—Entire.
*Base.*—Acute.
*Margin.*—Obtuse.
*Texture (both upper and lower surfaces).*—Smooth with fine hairs.

Reproductive organs:
*Androecium.*—Location: On disc and ray floret.
*Stamens.*—Quantity: Around 70. Shape: Filamentous. Filament length: 0.4 cm. Filament diameter: Less than 0.1 cm. Anther: Shape: Lanceolate. Color: RHS 77A (Purple). Length: 0.1 cm. Diameter: Less than 0.1 cm. Pollen: Color: RHS 17A (Yellow-Orange). Amount: Sparse.
*Gynoecium.*—Location: On the phyllary.
*Pistils.*—Number: Numerous, around 70. Length: 0.5 cm. Diameter: Less than 0.1 cm.
*Stigma.*—Color: RHS N77 (Purple). Shape: Filamentous, entire. Length: Less 0.1 cm. Diameter: Less than 0.1 cm.
*Style.*—Color: RHS NN155A (White). Length: 0.4 cm. Diameter: Less than 0.1 cm.

Fruit and seed set: None observed.

Disease and pest/insect resistance: No disease and pest/insect resistance observed.

COMPARISON WITH PARENTAL LINES AND KNOWN VARIETY

'KLEOE20555' is a distinct variety of *Osteospermum* and is distinguished from its parents as described in Table 1.

TABLE 1

Comparison with Parental Lines

| Characteristic | 'KLEOE20555' | Female Parent 'OE-2015-2178' | Male Parent 'OE-2014-1322' |
|---|---|---|---|
| Flower Color | Dark-purple | Purple | Dark-pink purple |

'KLEOE20555' is most similar to the commercial *Osteospermum* variety 'KLEOE16287' (U.S. Plant Pat. No. 30,135). Differences between the varieties are described in Table 2.

TABLE 2

Comparison with Similar Variety

| Characteristic | 'KLEOE20555' | KLEOE16287 |
|---|---|---|
| Branching | Good, a lot of branching | Not as much branching as 'KLEOE20555' |
| Flower quantity | High | Medium |

I claim:

1. A new and distinct variety of *Osteospermum* plant designated 'KLEOE20555' as illustrated and described herein.

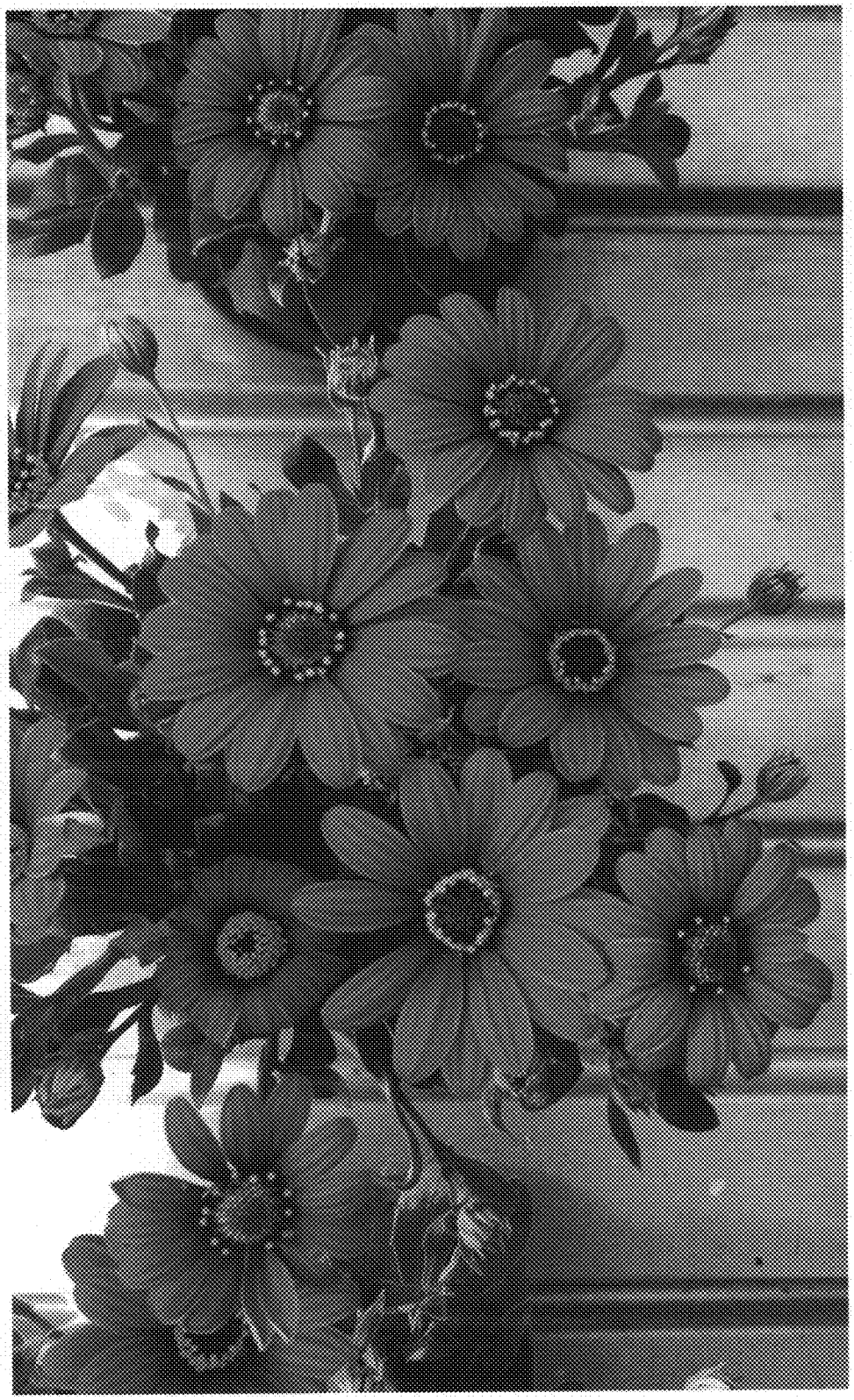

* * * * *